(12) United States Patent
Mazzio et al.

(10) Patent No.: US 7,357,950 B2
(45) Date of Patent: Apr. 15, 2008

(54) TOPICAL TREATMENT FOR DYSHIDROSIS (POMPHOLYX) AND DRY SKIN DISORDERS

(76) Inventors: Elizabeth Anne Mazzio, 982 W. Brevard St. D#22, Tallahassee, FL (US) 32304; Karam F Soliman, FAMU College of Pharmacy and Pharmaceutical Sciences 104 Dyson Building, Tallahassee, FL (US) 32307

( * ) Notice: Subject to any disclaimer, the term of this patent is extended or adjusted under 35 U.S.C. 154(b) by 0 days.

(21) Appl. No.: 10/801,520

(22) Filed: Mar. 16, 2004

(65) Prior Publication Data

US 2004/0185123 A1 Sep. 23, 2004

Related U.S. Application Data

(60) Provisional application No. 60/456,817, filed on Mar. 21, 2003.

(51) Int. Cl.
    *A61K 65/00* (2006.01)
    *A61K 31/74* (2006.01)
    *A61K 35/64* (2006.01)

(52) U.S. Cl. .................. 424/725; 424/771; 424/740; 424/754; 424/757; 424/729; 424/748; 424/744; 424/759; 424/730; 424/404; 424/78.03

(58) Field of Classification Search ............ 424/78.03, 424/404, 740, 730, 729, 757, 539, 754; 514/861, 514/863, 864
See application file for complete search history.

(56) References Cited

U.S. PATENT DOCUMENTS

| | | | |
|---|---|---|---|
| 4,631,295 A * | 12/1986 | Engel et al. | |
| 4,758,599 A * | 7/1988 | Minetti | |
| 5,057,501 A | 10/1991 | Thornfeldt | |
| 5,137,717 A * | 8/1992 | Wixforth | |
| 5,273,747 A * | 12/1993 | Bombardelli et al. | |
| 5,350,774 A | 9/1994 | Palou | |
| 5,859,066 A * | 1/1999 | Rosen | |
| 5,989,560 A * | 11/1999 | Terry et al. | |
| 6,248,343 B1 | 6/2001 | Jampani et al. | |
| 6,248,763 B1 | 6/2001 | Scivoletto | |
| 6,379,673 B1 | 4/2002 | Diwan et al. | |
| 6,395,261 B1* | 5/2002 | Laforet | |
| 6,403,654 B1 | 6/2002 | De Oliviera | |
| 6,517,846 B2 * | 2/2003 | Takekoshi | 424/401 |
| 6,528,071 B2 | 3/2003 | Vatter et al. | |
| 2003/0032617 A1 | 2/2003 | Bloch et al. | |
| 2003/0113388 A1 | 6/2003 | Phan | |

FOREIGN PATENT DOCUMENTS

| | | | |
|---|---|---|---|
| CN | 1360899 | | 7/2002 |
| DE | 10131641 | | 6/2002 |
| JP | 56071022 A | * | 6/1981 |
| JP | 143086 | | 6/1997 |
| JP | 157176 | | 6/1997 |
| JP | 11152212 A2 | * | 11/1997 |
| JP | 175878 | | 6/1998 |
| JP | 10158148 A | * | 6/1998 |
| JP | 10194938 A2 | * | 7/1998 |
| JP | 002559 | | 1/2001 |
| JP | 063942 | | 3/2003 |
| KR | 2001001823 A | * | 1/2001 |
| RU | 2118152 | | 8/1998 |
| RU | 2124363 | | 1/1999 |
| RU | 2131460 C1 | * | 6/1999 |
| WO | WO - 02/089826 | | 11/2002 |

OTHER PUBLICATIONS http://drclarkia.com/clarkia.asp, (Feb. 11, 2001), "CLARKIA Extra Strong". Accessed Nov. 22, 2004.*
Mabberley, D. J. The Plant-Book, 2nd edition, (1997). Cambridge University Press, United Kingdom, p. 469.*
http://www.itmonl.ine.org/arts/borneol.htm, (Sep. 1998). Dharmananda, S. Borneol, Artemisia, and Moxa. Accessed (Nov. 23, 2004).*
http://www.onelook.com/?w=moxa&ls=a, Nov. 23, 2004. OneLook Dictionary Search, "moxa".*
Xiao-fan, Zong et al. Chinese Medicinal Teas: Simple, Proven, Folk Formulas for Common Diseases & Promoting Health, 1996. Blue Poppy Press, pp. 136-137.*

* cited by examiner

*Primary Examiner*—Michele Flood

(57) ABSTRACT

A topical herbal formulation for preventing and/or treating dyshidrosis (pompholyx), non-responsive to topical steroids. The formulation may also be used to treat contact dermatitis, eczema, palmoplantar pustulosis and skin infections incurred by invasive pathogens such as mold, fungus and bacteria. The formulation is comprised of plant extracts and niacin, that when combined yield an effective multi-faceted pharmaceutical approach to treating dry skin disorders. The active ingredients within the formula include a combination of dry, aqueous, acid and alcohol extracts of black walnut hull (*Juglans Nigra*), wormwood (*Artemisia Absinthium*), tumeric rhizome (*Curcuma Longa*), garlic (*Allium sativum*), chamomile (*Matricaria Chamomile*), licorice root (*Glycyrrhiza Glabra*), St Johns wort (*Hypericum perforatum*), aloe vera, niacin and herbal anti-bacterial agents.

26 Claims, 2 Drawing Sheets
(2 of 2 Drawing Sheet(s) Filed in Color)

Experimental treatment for dyshidrosis - non-responsive to standard dermatology care or available prescriptive steroidal creams

TOPICAL TREATMENT FOR DYSHIDROSIS (POMPHOLYX) AND DRY SKIN DISORDERS

CROSS-REFERENCE TO RELATED APPLICATIONS

This application claims the benefit under 35 USC 119 (e), of a previous application. Ser. No. 60/456,817, filed on Mar. 21, 2003.

STATEMENT REGARDING FEDERALLY SPONSORED RESEARCH

Not Applicable

REFERENCE TO SEQUENT LISTING

Not Applicable

FIELD OF INVENTION

This invention describes a topical herbal formulation, useful for the prevention/treatment of dyshidrosis (pompholyx) or related skin disorders such as palmoplantar pustulosis, exfoliative keratolysis, contact dermatitis, eczema, ichthyosis and xerosis. The formulation is also lethal to fungus, mold, bacteria and yeasts, indicating potential to treat skin infections associated with invasive pathogens, such as dermatophyte fungi, staphylococci, streptococci, scabies, candida, aspergillus and scopulariopsis.

BACKGROUND OF INVENTION

Hand eczema is a prevalent skin disorder, encompassing a variety of diseases such as contact dermatitis and dyshidrosis (pompholyx) (Tamiya, Y. Nippon Ika Daigaku Zasshi 1994 61(4):286-94). Dyshidrosis is characterized by the initial symptoms of blistering and dry cracked skin on the hands or feet, affecting the tips and sides of fingers, toes, soles and palms. The disease develops progressively into continual scaling, peeling, cracked skin, bleeding, deep fissures and open wounds that do not heal. Dyshidrosis can exist as a chronic or recurring condition, and in some individuals it can persist for many years. Intermittent flare-ups tend to occur after extended periods of stress or emotional conflict. Although it is not known what causes the disease, dyshidrosis and other forms of hand dermatitis, are thought to be related to stress, anxiety or contact with some form of irritant or allergen (Lehucher-Michel, M. P., Koeppel, M. C., Lanteaume, A., Sayag, J. Contact Dermatitis 2000 43 (4):200-5).

While topical steroidal or non-steroidal immuno-suppressive agents remain the primary treatment for dyshidrosis, atopic dermatitis and psoriasis, they don't address the etiology of the disease and some individuals do not respond to prescriptive medicines. Moreover, local and systemic side effects are risks with extended use. If the condition is non-responsive to available medicine, lifestyle alterations for those suffering with pompholyx could include being confined to cotton lined gloves and avoiding direct contact with ubiquitous substances such as soap, water, detergents, paints, polish and chemicals. Moreover, there could be a potential loss of functional utility of the hands and/or feet. Open wounds require constant care to maintain aseptic conditions and apply bandages. And, since soap and water worsen the condition of this disease, it becomes quite difficult to maintain a sterile environment proximal to the site of injury.

Options available to those diagnosed with pompholyx or related skin diseases, who do not respond to steroidal anti-inflammatory agents are limited. The use of standard ultraviolet (UV) therapy (WO 02/055149, Oct. 22, 2001, Irwin and Altman) and subsequent modifications have been patented to treat dyshidrosis (U.S. Ser. No. 2002183811, Dec. 5, 2002, Irwin). The effects of UV therapy have been moderately successful, and in patients with non-responsive dyshidrotic eczema, approximately 31% establish complete remission, 33% exhibit partial remission and 36% exhibit no change (Douwes, K. E., Karrer, S., Abels, C., Landthaler, M., Szeimies, R. M. Photodermatol Photoimmunol Photomed 2000 16:25-9). For this reason, there is a need to investigate alternative topical agents to treat this and similar diseases of the skin, to which there are no effective treatments.

The embodied invention describes a useful formulation that can effectively establish remission of dyshidrosis, non-responsive to prescriptive topical medicine. These are preliminary findings, and warrant further research and investigation. To date, there are no integrated topical herbal formulas described to treat dyshidrosis or similar conditions such as exfoliative keratolysis and palmoplantar pustulosis. There are, however, patented therapeutic approaches described to treat dyshidrosis with vitamin E analogues (WO-97/45098, Jun. 02 1997, Panin), sulfhydryl acyl derivatives (U.S. Pat. No. 4,721,705, Jan. 26, 1988, Schreuder), oral administration of salts and esters of cis retinoic acid (U.S. Pat. No. 6,589,989, Jul. 8, 2003, Bollag, et al.) and topical steroids (U.S. Pat. No. 4,891,386, Oct. 15, 2002, Dykstra). Alternatives to treat pompholyx, have also included using an isolated extract derived from the bark of a southeastern Asian plant called the citrus decumana tree (JP-6340541, Dec. 13, 1994, Tashiro Eiichi) and fresh pine needle (CN-1113795, Dec. 27, 1995, Chunyang et al.).

The embodied invention discloses a novel topical formulation, found effective in establishing complete remission in a pilot trial of severe dyshidrosis, non-responsive to current prescription medicines and over the counter ointments. Moreover, the formula was found to be effective in rapidly suppressing and reversing initial symptoms of outbreak. Results indicate that therapy can be discontinued after remission is established. The principles governing development of the embodied formulation were based on observations regarding pathological symptoms of the disease: A) this skin disease stops at the perimeters of the hands and feet, indicating reduced circulation or blood flow may play a role B) this condition appears to involve an unknown factor, with an intermittent nature, that thrives on both moisture and flesh, possibly a virus C) this condition escapes capability of our immune system to destroy it and D) there is extensive skin loss, somewhat similar to a second degree burn. For these reasons, the topical ointment was formulated to (1) contain anti-microbial: anti-parasitic, anti-bacterial, anti-protozoal, anti-fungal and anti-viral properties to destroy or inhibit the growth of invading pathogenic organisms or potential unknown retroviruses (2) contain dermal anti-inflammatory agents: effective cyclooxgenase inhibitors/lipoxygenase inhibitors, and compounds that attenuate local dermal eicosanoids and prostaglandins to reduce the swelling, redness and pain (3) contain cutaneous vasodilators that inhibit thromboxanes, and increase local endothelial nitric oxide to increase blood flow to the area of injury (4) contain aloe vera gel as a base in order to promote rapid healing of damaged or lost skin tissue and (5) contain compounds that destroy or remove dead skin, which appear to correlate with rapid healing.

The embodied invention is unique, and its formulation was based on pharmacological scientific principles rather than literature describing common herbs that are good for the skin. While there are a number of herbal creams on the worldwide market available for the treatment of skin disorders, few contain the active ingredients as described in this invention. Moreover, it has been reported that many marketed herbal topical skin products, either don't work or they are misleading, claiming to be natural, but adulterated with potent steroids. Interestingly, according to an article on Tuesday, 9 Dec. 2003 BBC News Entitled "Steroids in herbal eczema creams", in a small scale study, 20 out of 24 herbal creams sold for treatment of eczema, contained potent steroid drugs, some labeled under the ingredient "Wau Wa", components that were really pharmaceutical grade steroids in a paraffin base. The reporter indicated that he would be surprised if any "herbal cream could rapidly eradicate eczema". There are also other reports that indicate a similar pattern where herbal creams sold over the counter, have been adulterated with agents such as topical zinc pyrithione or clobetasol propionate, which in some places are banned or illegal.

A review of the literature regarding skin creams that are sold and marketed, indicate that many herbal creams have analogous constituents, that are commonly known as skin remedies. Common ingredients in herbal skin creams include burdock, dandelion, lavender, marigold, marshmallow, nettle, violet, rosemary leaf, lemongrass, rosewood, sandlewood, yarrow, tea tree, geranium, chickweed, myrrh, yellow dock, golden seal, birch, calendula, echinacea, goldenseal, red clover, comfrey, and witch hazel or colloidal silver. Common herbal ointments include variations and combinations of these ingredients, such as, ZenMED natural eczema treatment system (zenmed-natural-herbal-eczema-treatment-cure.com), which contains the active ingredients borage oil, calendula, chamomile, viola, dog rose, echinacea, tea tree oil, vitamin A, C, E, bioflavonoids, kukui oil, lavender, geranium and tangerine. Another breakthrough herbal cream for eczema (Attogram Corp.), contains oils of cedarwood, chamomile, eucalyptus, lavender, palmarosa, rose, tea tree, castor, olive, colloidal silver, citric acid and lanolin. And, many variations have been described in herbal skin ointments such as combinations using comfrey, tea tree, witch hazel, dandelion, goldenseal, lavender, yellowdock (community-2.webtv.net), dandelion, goldenseal, red clover; yellow dock (sunthymeherbfarm.com), yellow dock, red clover or cleavers (viable-herbal.com), brewers yeast, nightshade and red clover (target.com), hawthorn, licorice, burdock, chamomile, ginkgo, gotu kola, echinacea, comfrey, dandelion, marshmallow, red clover etc. (herbs.org), goldenseal, kelp, myrrh, red clover, Pau d'arco, dandelion and yellow dock root (drcureme.com). The topical cream Florasone (herbalremedies.com) claims to be the first natural alternative to cortisone creams introduced in the United States and contains the active ingredient comprised of extract of Cardiospermum. And, other skin tonics such as those that treat herpes simplex, scabies, dermatitis, eczema and fungal infections are comprised of unique herbs such as cortex phellodendri, radix sophorae flavescentis, Rhuctus chidii and rhizoma atractylodis (herbalhealer.com).

According to a review of prior art, the embodied formula is novel in terms of its unique combination of powerful ingredients, and specific utility to ameliorate dyshidrosis and similar skin disorders such as palmoplantar pustulosis and exfoliative keratolysis. The primary ingredients within the formula include a combination of dry, aqueous, acid or alcohol extracts of black walnut hull (*Juglans Nigra*), wormwood (*Artemisia Absinthium*), tumeric rhizome (*Curcuma Longa*), garlic (*Allium sativum*), chamomile (*Matricaria Chamomile*), licorice root (*Glycyrrhiza Glabra*), St Johns wort (*Hypericum perforatum*), aloe vera, niacin or its derivatives and one or more herbal antibacterial agents. This combination of ingredients, as a composite, was also found to be lethal to bacteria, fungus, mold and yeast, indicating its use may include an expansive range of skin disorders associated with invasive pathogens. The formula is comprised of cooking spices and components that are often taken orally by humans, therefore the ingredients should be relatively safe, with exception of potential allergic sensitivity reactions that may occur. The following is an introduction of circumscribing prior art for each ingredient in the formula as it applies to topical applications of the skin.

INGREDIENT 1: Extracts of wormwood or artemesia are often incorporated into complex formulas that comprise agents directly applied to the skin, such as aftershave lotion (RU-2109506, Apr. 27, 1998 Dolotovskij et al.,), facial cleanser (RU-2124350, Jan. 10, 1999, Detsina et al.,; CN-1236610, Dec. 1, 1999, Liu), wrinkle reduction cream (CN-1110132, Oct. 18, 1995, Zhongxin), muscle pain ointment (U.S. Pat. No. 6,579,543, Jun. 17, 2003, McClung), treatment for warts (U.S. Pat. No. 5,576,005, Nov. 19, 1996, Wise, et al.) and anti-aging formulas that promote synthesis of collagen (JP-206835, Jul. 31, 2001, Sasaki et al.).

Wormwood is known for its anti-parasitic effects, and if taken internally can promote bowel movement, improve digestion and enhance blood circulation. Previous research on therapeutic use for wormwood and artemisinin, primarily focus on its efficacy as an anti-malarial compound. There is little to no technical research, documenting the efficacy of wormwood, relevant to skin diseases. There are, however, topical agents patented for treatment of dry skin that have included wormwood as a minor component in a list of ingredients. Of these include: wormwood 1) listed with 12 other herbal constituents that comprise a secondary tincture to be combined with a primary herbal extract base consisting of rowan melanocarpous, bird cherry and rose fruit, and a pretreatment of Siberian fir coniferous needles and sea-buckthorn juice for treatment of dermatitis (RU-2124363, Jan. 10, 1999, Tereshchenko et al.,) 2) in combination with pine needle, dark plum, peppermint, acetic acid, borneol and bezoar, for treatment of dermatitis (CN-1360899, Jul. 31, 2002, Lan) 3) artemisia capillaris incorporated in to a base formula of ω3 and ω6 fatty acids as one of approximately 30 optional herbal extracts to treat dry skin, inflammation, rash and itching (JP-063942, Mar. 5, 2003, Shizuka et al.,) and 4) at very low concentration, (approx 0.1-0.5% wormwood) in combination with glycerine, propolis extract, oil of common origanum, polyethyleneoxide gel, egg yolks, horsetail decoction, bergenia, plantain, citric, salicylic acids, henx salts, benzoate for treatment of fungal and microbial infections of the skin (RU-2118152, Aug. 27, 1998, Detsina et al.). It has been reported that the tricyclic sesquiterpene, artemisinin and its derivatives (chemicals found naturally in wormwood) may be effective in treating psoriasis, dermatitis, dyshidrosis and eczema (U.S. Pat. No. 5,057,501, Oct. 15, 1991, Thomfeldt). These findings indicate that beneficial effects observed in treatment of pompholyx, may be due to artemisinin and related chemicals within the extract of wormwood.

INGREDIENT 2: Black walnut (*Juglans Nigra*). While the toxicity of black walnut in equine has been investigated, there is little to no research documenting the use of *Juglans Nigra* to treat either infectious or non-infectious skin disorders. Further, there is meager patent literature describing the use of black walnut or *Juglans Nigra* incorporated into topical creams or cosmetics, with exception of its use as a germicidal agent incorporated into chewing gum, deodorant gel and foot powder (U.S. Pat. No. 5,137,717, Aug. 11, 1992, Wixforth). Although there is little documentation in either research or patented literature, historical herbal literature indicates that black walnut is known to treat intestinal parasites, worms, warts, growths, eczema, psoriasis, lupus, herpes, and skin parasites. Interestingly, black walnut is not a common ingredient amongst herbal preparations marketed or sold for treatment of skin.

INGREDIENT 3: St. John's wort (*Hypericum perforatum*) is often incorporated into topical formulas that comprise weight loss cream (U.S. Pat. No. 4,795,638, Jan. 3, 1989, Ayache et al.), anti-aging cosmetic (U.S. Pat. No. 4,911,925, Mar. 27, 1990, Shatkina et al.), lotion (EP-1291011, Mar. 12 2003, Leonidov et al; RO-116865, Jul. 30, 2001, lonita-Manzuta et al.), facial cleanser (U.S. Pat. No. 6,342,208, Jan. 29, 2002, Hyldgaard et al.), topical treatment for acne and chapped skin (JP-04-124138, Apr. 24, 1992, Yan et al.), bum ointment (CN-1179950, Apr. 4, 1998, Mo Xiaochun), treatment for fungal infections of the nail (GB-2311009, Sep. 17, 1997, Khan Mohd Taufiq) muscular pain relief lotion (U.S. Pat. No. 6,579,543, Jun. 17, 2003, McClung), arthritis pain reliever (U.S. Pat. No. 6,573,302, Jun. 3, 2003, Holt et al.), moisturizer (JP-60-258104, Dec. 20, 1985, Yuchi et al.,) and lotions with smoothing, firming and UV protection properties (U.S. Pat. No. 5,560,917, Oct. 1, 1996, Cohen et al.).

St. John's wort has also been used in the past, as a remedy to treat wounds and burns (Schempp C M, Muller K A, Winghofer B, Schopf E, Simon J C. Hautarzt. 2002 May; 53(5):316-21). Hyperforin, a primary constituent of St. John's wort is effective in treating atopic dermatitis (Schempp C M, Windeck T, Hezel S, Simon J C., Phytomedicine. 2003;10 Suppl 4:31-7.), possibly through anti-inflammatory properties (Schempp C M, Winghofer B, Ludtke R, Simon-Haarhaus B, Schopf E, Simon J C., Br J Dermatol. 2000 May;142(5):979-84.). St. John's wort has also been used as a constituent in topical agents for treatment of dry skin as it relates to photo damage effects of the sun. Of these, include its use in combination with branches and leaves of olive, glycyrrhetinic acid and allantoin (JP-183146, Jul. 03, 2003, Hikima et al.) and in combination with asparagus extract, chamomile, *Lithospermum erythrorhizon*, *Lonicera japonica*, sage, birch, *Calendula officinalis*, elder tree, flag, glycyrrhizic acid, guaiazulene, aminocaproic acid and their derivatives (JP-06-128145, May 10, 1994, Hayashi et al.).

Relevant prior art pertaining to the use of St. John's wort include 1) the use of extracts of St John's wort depleted of chlorophyll for treatment of acne, viral infections and psoriasis (DE-10131641, Jun. 27, 2002, Koch et al.,) 2) its use with or without *Tilia miqueliana* extract to treat contact dermatitis, allergic skin reactions and rough skin (JP-09-157176, Jun. 17, 1997, Nishibe) and 3) St. John's wort added to a base formula of co3 and co6 fatty acids, as one of 30 optional herbal extracts to treat dry skin, inflammation, rash and itching (JP-063942, Mar. 5, 2003, Uehara Shizuka et al.).

INGREDIENT 4: TURMERIC (*Curcuma Longa*) has been incorporated into topical skin lightening and UV protective lotion (WO 03/030814, Apr. 17, 2003, Muhammed et al.), treatment for acne (CA-2353057, Jan. 13, 2002, Khaiat; U.S. Pat. No. 6,277,881,Aug. 21, 2001, Santhanam et al.), treatment for skin discoloration and hemorrhoids (U.S. Pat. No. 6,048,533, Apr. 04, 2000, Nguyen Van Bich), ointment that relieves soreness and muscle discomfort (U.S. Pat. No. 6,579,543, Jun. 17, 2003, McClung), lotion that protects against environmental toxins (U.S. Pat. No. 6,521,668, Feb. 18, 2003, Anderson et al.) and treatment for wounds and ulcers (U.S. Pat. No. 5,401,504, Mar. 28, 1995, Das et al.).

Turmeric is an anti-inflammatory agent and when applied to the skin, has shown to reduce dermal inflammatory promoters such as arachidonic acid, cyclooxygenase, lipoxygenase 5-hydroxyeicosatetraenoic acid and pro-inflammatory prostaglandins (Huang, M. T., Lysz, T., Ferraro. T., Abidi, T. F., Laskin, J. D., Conney, A. H. Cancer Res 1991 51:813-9.; Huang, M. T., Newmark, H. L., Frenkel, K. J Cell Biochem Suppl 1997 27:26-34). Curcumin also contains inherent antiviral properties (Barthelemy, S., Vergnes, L., Moynier, M., Guyot, D., Labidalle, S., Bahraoui, E. Res Virol 1998 January-February;149(1):43-52; De Clercq, E.Med Res Rev 2000 20:323-49) and is effective against tumor promoting viral agents, such as Epstein-Barr virus and herpes simplex virus type 2 (Kapadia, G. J., Azuine, M. A., Tokuda, H., Hang, E., Mukainaka, T., Nishino, H., Sridhar, R. Pharmacol Res 2002 45:213-220.; Boume, K. Z., Boume, N., Reising, S. F., Stanberry, L. R. Antiviral Res 1999 42:219-26). Moreover, turmeric has a number of other pharmacological properties such as anti-bacterial, anti-parasitic and antispasmodic (Araujo, C. C., Leon, L. L. Mem Inst Oswaldo Cruz 2001 96:723-8).

Prior art describing the use of turmeric as a constituent in topical agents for treatment of dry skin include: its use as a minor ingredient 1) in combination witn hydroxy acids, vitamin E, vitamin B, glycolic acid, antioxidants, hormones, and oils to treat psoriasis, dryness, itching, stretch marks, and microbial infections (U.S. application Ser. No. 2003113388, Jun. 19, 2003, Phan) 2) in combination with triclosan, phenoxy ethanol, benzalkonium chloride, benzethonium chloride, cocophosphatidyl-dimonium chloride for the treatment of skin inflammations, redness, pain, exudate, and bacterial infections (U.S. Pat. No. 6,248,343, Jun, 19, 2001, Jampani et al.), 3) at a low concentration (0.1-1%), as an optional anti-inflammatory compound incorporated into a base of carbopol, emulsifiers, preservatives, and humectants containing Tridax procumbens extract and gum olibanum powder the treatment of cracked heels, dry skin disorder, skin allergies, depigmentation, burns, wounds and fungus (U.S. Pat. No. 6,379,673, Apr. 30, 2002, Diwan et al. ) 4) in combination with ω3 and ω6 fatty acids for treating dry skin, inflammation, rash and itching (JP-063942, Mar. 5, 2003, Uehara Shizuka et al.,) 5) incorporated as an optional ingredient selected from a list of herbs into a base of dihydric alcohol solution, as an antibacterial skin preparation (JP-145793, Mar. 22, 2002, Kobayashi Kayoko et al.,) and 6) in combination with a base comprising hydroxy acid and retinol deriviatives, for treating skin inflammation and irritation (JP-002559, Jan. 9, 2001, Santanamu et al.,). In documents where turmeric comprises a primary component, (JP-09-143086, Jun. 3, 1997, Masayoshi), a fat-soluble extraction procedure for turmeric has been described, introducing a carrier system of vegetable oil for treatment of skin diseases such as eczema, acne, atopic dermatitis, chapped skin or general.

INGREDIENT 5: Propolis is an optional ingredient in this formula. It was not incorporated into the base formula as tested, however, it may be used as a substitute to replace ingredients that may otherwise cause allergic skin reactions such as garlic, or to enhance efficacy or aesthetic properties. Propolis has been used in formulations that comprise beauty lotion, or regenerative skin cosmetic (RU-2166313, May, 10, 2001, Dolotovskij et al.), deodorizer (RU-2185808, Jul.

27, 2002, Khismatullin), moisturizing cream (RU-2161029, Dec. 27, 2000, Kravchenko; JP-10-194948, Jul. 28, 1998, Yamamoto), wrinkle removing cream (RU-2161029, Dec. 27, 2000, Zhang; CN-1268348, Oct. 4, 2000, Tong), bug repellent, skin cleanser, germicide (CN-1263146, Aug. 16, 2000, Liu Fuhai Xu et al.) exfoliation cream (U.S. Pat. No. 6,416,769, Jul. 9, 2002, Vromen), skin whitener (U.S. Pat. No. 6,269,817, Aug. 7, 2001, Nagashima et al.) tanning solution (U.S. Pat. No. 6,171,605, Jan. 9, 2001, Bevacqua et al.) bum ointment (JP-07-304684, Nov. 21, 1995, Longchamp), treatments for acne and dandruff (JP-59-118702, Jul. 9, 1984, Takashi et al.) and treatment for skin fungal infections, such as candidiasis (RU-2118152, Aug, 27, 1998, Detsina).

There is documented evidence that topical application of propolis can aid in the healing of bum wounds (Gregory, S. R., Piccolo, N., Piccolo, M. T., Piccolo, M. S., Heggers, J. P. J Altern Complement Med 2002 8:77-83). Moreover, propolis has several medicinal properties, including it ability to serve as an analgesic, anti-flammatory agent, and ameliorate symptoms of psoriasis (Ledon, N., Casaco, A., Gonzalez, R., Merino, N., Gonzalez, A., Tolon, Z. Zhongguo Yao Li Xue Bao 1997 18:274-6; Park, E. H., Kahng, J. H. Arch Pharm Res 1999 22:554-8). Propolis is also a powerful antibacterial and antifungal agent, with efficacy demonstrated against a large variety of pathogens (Ota, C., Unterkircher, C., Fantinato, V., Shimizu, M. T. 2001 44:375-8; Drago, L., Mombelli, B., De Vecchi, E., Fassina, M. C., Tocalli, L., Gismondo, M. R. J Chemother 2000 12:390-5; Koo, H., Gomes, B. P., Rosalen, P. L., Ambrosano, G. M., Park, Y. K., Cury, J. A. Arch Oral Biol 2000 45:141-8).

Propolis as a constituent has been used in topical agents for treatment of dry skin and/or bacterial infections, some of which include its use 1) in combination with an inert base, arnica montana, woody aloe, marigold and at least one antibiotic selected from detromycin, bacitracin, neomycin, polymyxin etc. for ameliorating burns (WO 02/076411, Oct. 3, 2002, Dorian) 2) in combination with olive oil, sea buckthorn-seed oil, beeswax, dog rose oil, St. Johns wort oil extract, peony root oil extract, bergenia oil extract to treat wounds (RU-2195258, Dec. 27, 2002, Repjakh) 3) in combination with honey, apricot seed extract and royal jelly to treat discoloration, wounds, burns, miliaria and eczema (KR-20010008260 A, May 2, 2001,Kim), 4) in combination with Balsaminaceae to treat skin allergies and atopic dernatitis (JP-11-322620, Nov. 24, 1999, Sakamoto et al.) 5) in combination with pyrolignous acid, chitin chitosan and garlic for treatment of parasitic atopic dermatitis, athlete's foot, scabies, dermatophytosis, candidiases, scabies, tinea cruris or serpigo (JP-10-175878, Jun. 30 1998, Otsuka et al.) and 6) in combination with alcoholic-glyceric nettle, chelidonia, oak bark, willow bark, calendula, dandelion roof, camomile, achillea, dill, parsley, thyme oil, lemon oil etc, for treatment of psoriasis (WO 01/66079, Feb. 28 2001, Bodnar et al.).

INGREDIENT 6: Chamomile (*Matricaria Chamomile*) has been incorporated into topical anti-pollution cream (U.S. Pat. No. 5,571,503, Nov. 5, 1996, Mausner), a cosmetic (U.S. Pat. No. 6,299,890, Oct. 9, 2001, Russ et al.), lotion (U.S. Pat. No. 6,589,514, Jul. 8, 2003 Jensen et al.), moisturizer (U.S. Pat. No. 6,579,516, Jun. 17, 2003, Mansouri), tanning solution (U.S. Pat. No. 6,482,397, Nov. 19, 2002, Scott et al.), exfoliation cream (U.S. Pat. No. 6,416,769, Jul. 9, 2002, Vromen), anti-aging and whitening cream (U.S. Pat. No. 5,393,526, Feb. 28, 1995, Castro), skin cleanser (U.S. Pat. No. 6,221,372, Apr. 24, 2001, Golz-Bemer et al.) acne treatment (CA-2353057, Jan. 13, 2002, Khaiat), revitalizing, smoothing, moisturizing cream (U.S. Pat. No. 5,876,736, Mar. 2, 1999, Cohen et al.), arthritic pain reliever (U.S. Pat. No. 5,869,533, Feb. 9, 1999, Holt), cuticle and nail ointment (WO 03/047537, Jun. 12, 2003, Beaurline) and aftershave lotion (U.S. Pat. No. 4,758,599, Jul. 19, 1988, Minetti).

Chamomile has been incorporated into topical agents with dozens of other ingredients, for treatment of dry skin disorders. These include its use 1) in combination with *Althaea officinalis L.*, Malva flowers, *Tillia Platyphyllos* and *Achillea millefolium* L. for treatment of skin inflammation, excoriations, ulcers (WO 03/033007, Apr. 24, 2003, Baraldi) 2) in combination with *Chelidonium majus* L, *Plantago major* L, *Plantago media* L, *Convallaria majalis* L, may flower honey, raw egg, gum-tree oil, lanolin for treatment of atopic dermatitis, urticaria and eczema (RU-2107510, Mar. 27, 1998, Labutin et al) 3) in combination with propylene glycol, acids, alcohols, carbomer, tea tree, amino acids, etc., for treating psoriasis (U.S. Pat. No. 6,403,654, Jun. 11, 2002, De Oliveira) 4) in combination with plantago major, yarrow, olive oil, eucalyptus, calendula for treatment of burns and wounds (U.S. Pat. No. 5,997,876, Dec. 7, 1999, Shikhashvili et al.) and 5) in combination hamamelis, almond oil, olive oil, and myrrh with for treatment of abrasions broken skin,cuts, cold sores, bed sores and piles (U.S. Pat. No. 5,350,774, Sep. 27, 1994, Palou).

INGREDIENT 7: Garlic (*Allium Sativum*) or deodorized garlic has been incorporated into weight loss cream (U.S. Ser. No. 2002146474, Oct. 10, 2002, Tomatis), anti-aging cream (KR-2002019716, Mar. 13, 2002, Choi et al.), depilatory cream (CN-1398578, Feb. 26, 2003, Wu), general skin protective lotion (CN-1378835, Nov. 13, 2002, Gu et al.), an analgesic (U.S. Pat. No. 6,579,543, Jun. 17, 2003, McClung) rejuvenation cream (JP-09-328417, Dec, 22 1997, Morinaga), body rinse (JP-08-165233, Jun. 25, 1996, Kuroiwa et al.), moisturizer (JP-07-133208, May, 23, 1995, Okada) skin peel (JP-54044082, Apr. 7, 1979, Tsukada et al.) and treatment for head lice (U.S. Pat. No. 6,103,248, Aug. 15, 2000, Burkhart et al.) and hairloss (U.S. Pat. No. 4,855,131, Aug. 8, 1989, Iris).

The effects of garlic on the skin have been reported specific to psoriasis. For example, (US-U.S. Pat. No. 6,153, 197, Nov. 28, 2000, Albazi et al.) discloses a mixture of garlic and radish plant in dilute acetic acid to treat psoriasis. Garlic in combination with plumbago europaea (DE-10126023, Dec. 12, 2002, Karassalidou-Mueller) and urtica dioica, common nettle/chelidonium majus, milkweed, veronica officinalis, veronica, calendula officinalis. calendula or marigold, achillea herba, millefolium, yarrow, fumaria officinalis are also effective against psoriasis (U.S. Pat. No. 5,165,932, Nov. 24, 1992, Horvath). And, mixtures of garlic with oil of celery seed, ceresin, Tween 80, castor oil and salicylic acid have been described for treatment of psoriasis (GB-842404, Jul. 27, 1960, Braun Ernest).

Garlic has been incorporated into topical agents with a list of other ingredients, for treatment of dry skin disorders. These include its use 1) as an optional ingredient amongst others in a base mixture with eperisone and tolperisone for the treatment of itching and dermatitis (JP-143513, May, 23, 2000, Manabe) 2) as an oil form (1-3% wt), incorporated into a base gel containing carbopol, emulsifiers, preservatives, humectants, anti-inflammatory compounds and optional ingredients such as Tridax procumbens extract and gum olibanum powder for treatment of cracked heels, dry skin disorders and skin allergies (U.S. Pat. No. 6,379,673, Apr. 30, 2002, Diwan et al.) 3) its use as a primary ingredient to treat infectious skin diseases (WO 02/089826, Nov. 14, 2002, Bhatham et al.,) and 4) in combination with propolis, pyroligneous acid and chitin to treat a large range of skin infections including, dermatophytosis, candidiases, scabies, tinea and others (JP-175878, Jun. 30, 1998, Otsuka Yuzaburo et al).

INGREDIENT 8: Licorice (*Glycyrrhiza Glabra*) has been incorporated into topical agents have been described for treatment of acne (CN-1377686, Nov. 6, 2002, Zhang; JP-11-100324, Apr. 13, 1999, Sugimoto et al.), burn and sunburn ointment (CN-1348789, May, 15, 2002, Yang), protection against environmental aggressors (U.S. Pat. No. 6,649,178, Nov. 18, 2003, Mohammadi et al.), cleanser (JP-096492, Apr. 3, 2003, Suzuki), an anti-aging formula (JP-034631, July, Feb, 7, 2003, Honda; JP-370960, Dec, 24 2002, Ueno et al.), a whitening agent (JP-284626, Oct, 03, 2002, Miki; JP-247442, Sep. 11, 2001, Maeda et al.), collagen synthesis promoter (JP-206835, Jul. 31, 2001, Sasaki et al.) and makeup (JP-09-052814, Feb. 25, 1997, Futaishi).

Licorice has steroidal like properties, and for that reason, should be incorporated into the formula with discretion. Licorice has been previously incorporated into topical agents with dozens of other ingredients, for treatment of dry skin disorders. These include its use 1) in combination with almond extract, sterol esters of a 10-26C α-hydroxy fatty acid (JP-255780, Sep. 11, 2002, Yamashita) 2) with siberian fir coniferous needles, sea-buckthorn juice, rowan melanocarpous, and many other herbal components (RU-2124363, Jan. 10, 1999, Tereshchenko et al.) 3) with tannic acid and carrageenan (U.S. Pat. No. 5,198,217, Mar. 30, 1993, Vedros) 4) with extracts of Marigold, Horse-chestnut, silverweed, Walnut-tree leaves, Lavender and Roman chamomile oil (U.S. Pat. No. 5,080,901, Jan. 14, 1992, Ranky Nee Szita Katalin et al.) 5) with hydrocarbons, esters, triglycerides, fatty acids, surfactants, antiseptics, ultraviolet absorbers (JP-10-194949, Jul. 28, 1998, Sugiyama et al.) and 6) with extract of *Sarcodon aspratus* (Berk.) S. stearyl glycyrrhetate and dipotassium glycyrrhetate (JP-151689, Jun. 05, 2001, Kawamoto et al.).

INGREDIENT 9: Niacin, has been incorporated into cosmetics and other topical applications such as weight loss cream (WO 98/00101, Jun. 27 1997, Pinotti et al.,), arthritic pain relief ointment (U.S. Ser. No. 2003125303, Jul. 3, 2003, Kucharchuk), skin lightening agent (U.S. Pat. No. 4,096, 240, Jun. 20, 1978, Mathur; CA-2147262, May 11, 1994, Harding et al.,) pigmentation formula (JP-, 10-059839, Mar. 03, 1998, Imahori), UV protectants (WO 02/03942, Jul. 6, 2001, Barclay), aftershave lotion (U.S. Pat. No. 4,758,599, Jul. 19, 1988, Minetti) and treatment for acne (GB-2210789, Jun. 21, 1989, Morrison), chapped skin, aging (JP-63-174911, Jul. 19, 1988, Sato; CA-2251790, Oct. 30, 1997, Oblong et al.) and dandruff (JP-63-060910, Mar. 17, 1988, Kawajiri et al.,).

Synthesized esterified nicotinamide derivates have been described for treatment of many diseases including cardiovascular, inflammatory, dermatological disorders, baldness, diabetes, cancer, and a method for the management of chemotherapy (NZ-306510, Jan. 18, 2000, Redden et al. and CA-2220091, Nov. 7, 1996, Manku et al.). Moreover, niacin has been used in conjunction with other constituents in topical agents to treat dry skin disorders. These include its use 1) in combination with nitrous oxide, essential fatty acids and *Liquor Picis Carbonis* [coal tar] to treat psoriasis, shingles, fever blisters, chicken pox, ache, chilblains, eczema, chloasmas, alopecia, dermatitis, ringworm and bum wounds (U.S. Pat. No. 5,633,284, May 27, 1997, Meyer) and 2) in combination with methylparaben, coconut oil, glycerine, polysorbate 60, vitamins etc, for treatment of psoriasis (CA-2027600, Apr. 16, 1992, Tosti).

Relevant art describing the use of niacin as the primary active constituent in topical formulations to treat skin disorders include its use as 1) esters of nicotinamide and nicotinic acid for treatment of acne, wrinkles, age spots, itching, pain, fungal infections, flaky dry skin, dandruff, seborrheic dermatitis, psoriasis and burns (U.S. Pat. No. 6,248,763, Jun. 19, 2001, Scivoletto) 2) as nicotinamide analogs to treat psoriasis, ichythyiosis, common warts, keratoacanthoma, seborrhoic keratosis and seborrhea (U.S. Ser. No. 2003032617, Feb. 13, 2003, Bloch et al.) 3) niacin derivatives where delivery has been improved for penetration into the skin (U.S. Pat. No. 6,528,071, Mar. 4, 2003, Vatter et al.) and 4) incorporated into emulsions of microparticulates containing vitamin B3 for better delivery (U.S. Pat. No. 6,551,604, Apr. 22, 2003, Beck et al.).

INGREDIENT 10: Aloe has well known effects on the skin, including positive effects on cell regeneration and growth of epidermal tissue. (Choi, S. W., Son, B. W., Son, Y. S., Park, Y. I., Lee, S. K., Chung, M. H. Br J Dermatol 2001 45:535-45). Aloe can increase blood flow to the skin, and promote rapid healing of damaged skin tissue (Somboonwong, J., Thanamittramanee, S., Jariyapongskul, A., Patumraj, S. Med Assoc Thai 2000 83:417-25; Visuthikosol, V., Chowchuen, B., Sukwanarat, Y., Sriurairatana, S., Boonpucknavig, V. J Med Assoc Thai 1995 78:403-9). One of the major therapeutic properties of aloe, include its ability to increase collagen, dermatan sulphate and glycosaminoglycans (Chithra, P., Sajithlal, G. B., Chandrakasan, G. Mol Cell Biochem 1998 181:71-6; Chithra, P., Sajithlal, G. B., Chandrakasan, G. Indian J Exp Biol 1998 36:896-901; Chithra, P., Sajithlal, G. B., Chandrakasan, G. J Ethnopharmacol 1998 59:179-86).

SUMMARY OF INVENTION

The following discloses an all natural topical formulation for treatment of dyshidrosis, and potentially other dry skin disorders such as eczema, dermatitis or psoriasis. The formula is comprised of a unique combination of extracts derived from natural plants and herbs, containing, antimicrobial, anti-parasitic, anti-bacterial, anti-protozoal, antifungal, anti-viral, anti-inflammatory and vasodilatory properties. The primary active ingredients in the formula include aqueous, acid and alcohol extracts of: black walnut (*Juglans Nigra*), wormwood (*Artemisia Absinthium*), tumeric rhizome (*Curcuma Longa*), garlic (*Allium sativum*), chamomile (*Matricaria Chamomile*), licorice root (*Glycyrrhiza Glabra*), St Johns wort (*Hypericum perforatum*), aloe vera, niacin and optional herbal anti-bacterial agents.

BRIEF DESCRIPTION OF THE DRAWINGS

The patent or application filed contains at least one drawing executed in color. Copies of this patent or patent application publication with color drawings will be provided upon request and payment of necessary fee.

DETAILED DESCRIPTION OF THE PREFERRED EMBODIMENT

The following discloses a formulation for treatment of dyshidrosis, and other dry skin or infective skin disorders. The formula is comprised of a combination—selected from the group of active ingredients consisting of aqueous, acid or alcohol extracts black walnut (*Juglans Nigra*), wormwood (*Artemisia Absinthium*), turmeric rhizome (*Curcuma Longa*), garlic (*Allium sativum*), chamomile (*Matricaria Chamomile*), licorice root (*Glycyrrhiza Glabra*), St Johns wort (*Hypericum perforatum*), niacin, aloe vera alone or in combination with dermatologically acceptable carrier and optional herbal anti-bacterial agents such as nutmeg, myrrh or clove. The demonstrated utility of the embodied invention should not be interpreted to limit the scope of the invention with regards to application, use or treatment as it relates to skin disorders of analogous symptomatic pathologies.

Figure 1:
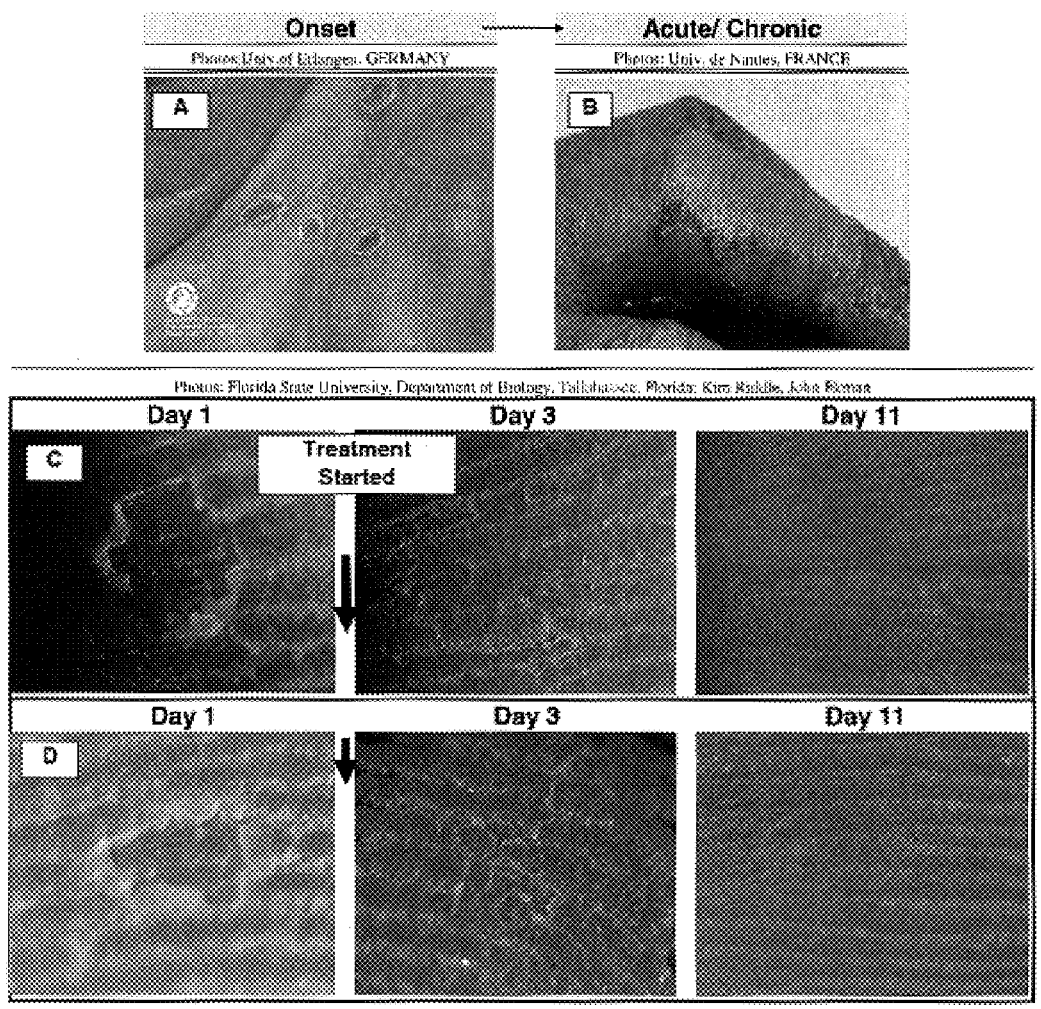
FIGS. 1A,B are diagnostic photographs demonstrating the symptoms of dyshidrosis at onset (initial outbreak) and development into an acute or chronic condition.
FIGS. 1C,D demonstrate the effect of the topical treatment on halting dyshidrosis disease progression and establishing remission. Photographs of the initial outbreak $2^{nd}$ day=Day 1 are depicted in the left hand panel. Topical application was initiated on Day 1, and follow up photos were taken at Day 3 (middle panel) and Day 11 (right panel). At Day 11, complete remission was established.
FIGS. 1E-G demonstrate a gradual worsening of dyshidrosis on skin sections left without treatment from Day 1 to Day 2. At the end of the $2^{nd}$ day, treatment was initiated, and photos were taken on Day 3 (left panel) and Day 11 (right panel), where complete remission was established.
Figure 1:
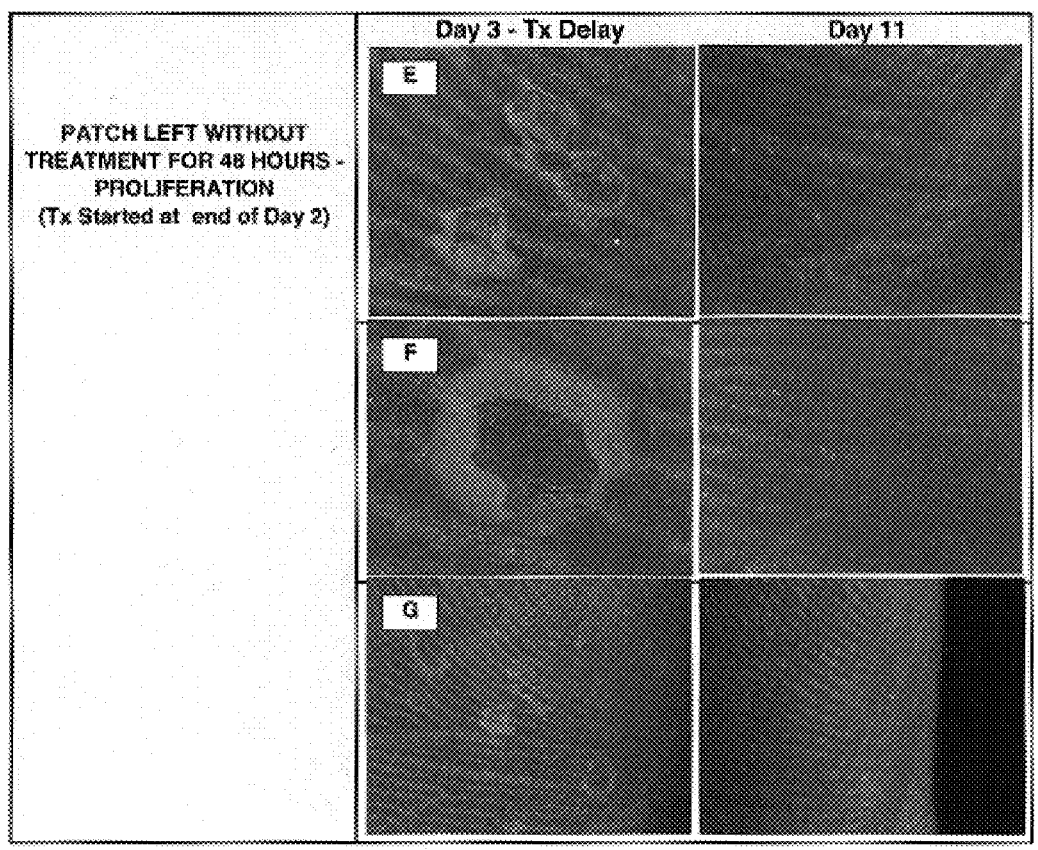

The practical utility of this invention was demonstrated in a case study of a patient diagnosed with classic dyshidrosis, non-responsive to prescriptive topical applications. The initial symptoms of the disease appeared as little white blister formations on the patients hands, that proliferated rapidly in number and area, spreading down the fingers and toward the palms on both hands. Despite daily therapy with prescriptive topical steroids, the condition worsened rapidly and within a short period of time (~1 month), there was extensive peeling, cracked dry skin, skin loss, scales, fissures, open wounds and bleeding. Gradual worsening and non-healing of skin tissue was similar to and approaching the condition as depicted in a standard diagnostic photograph of developed dyshidrosis (FIG. 1A,B). The skin on the finger tips of this patient was completely gone, and fingerprints were indistinguishable. The patient was confined to wearing white cotton gloves, bandages, and was restricted from contact with soap and water. Prescription medications were ineffective, and any type of moisturizing cream could not be applied, without causing pain. The condition was debilitating and resulted in the loss of use of both hands. With gradual worsening, the patient also tried several over the counter triple antibiotic ointments and anti-fungal agents, all of which were ineffective. All medications were discontinued and the formulation as described in this embodiment was applied topically.

Within a week, the body's natural skin moisture appeared to be restored. The redness, pain and bleeding had stopped, and the skin started to heal. Due to extensive skin loss,— equivalent to a $2^{nd}$ degree burn, the healing time was dependent upon the extent of skin loss, where the inherent nature of the disease appeared to be eliminated. Complete recovery was achieved in a relatively short period of time, and treatment was discontinued. The patient now lives free from this disease, and any flare-up can be rapidly eradicated with the embodied invention. Individuals, that do not respond to treatment, often live with this disease, for years to decades. In a follow up investigation, on two separate occasions within the next several years, approximately 5-10 little white blister formations emerged on the finger tips of the patient, synonymous with initial symptoms of a relapse (See FIGS. 1C-G). The topical agent was immediately applied and found to be effective in halting the outbreak and establishing remission. One finger was left untreated for 48 hours, and exhibited progressive blister formation (FIGS. 1C-E), which could rapidly deteriorate into a serious condition as demonstrated in FIG. 1A. Upon treatment, the skin was rapidly restored to its normal healthy tissue, corroborating that therapeutic effects were due directly to the treatment, and not a spontaneous remission.

Because the treatment was effective in both halting and reversing an acute progressive disease state, the findings warrant further investigation to evaluate efficacy and variation of this formula to treat not only pompholyx, but similar dry skin disorders. Moreover, the formulation as a composite, was evaluated for toxicity to invasive pathogens. And, at extremely dilute concentrations (<1% of working concentration), the formulation was lethal to bacteria, fungus, mold and yeasts such as *Streptococcus pneumoniae, Candida parapsiolosis, Cryptococcus neoformans* and *Aspergillus fumigatus*. These findings indicate a potential beneficial effect against skin disorders that are initiated by invasive pathogens.

The formulation is to be applied topically, and its utility is for the prevention and/or treatment of pathological conditions of the skin. Pathological conditions of the skin, herein referred to as "pathological conditions" "conditions", "skin conditions" and "skin disorders" are defined as symptoms present anywhere on the skin, characterized by mild or extremely dry skin, skin lesions, cracks, fissures, scaling, discoloration, thickening, redness, bleeding, swelling, flaking, ulcers, sores, wounds, blistering, rashes, loss of flesh or similar. In particular, these would include skin disorders that affect the feet and hands, such as pompholyx, palmoplantar pustulosis and keratolysis exfoliativa.

The aforementioned pathologies also include "skin disorders" classified under dermatitis including but not limited to: atopic, contact, hand, allergic, gravitational, asteatotic, nummular, seborrhoeic, infective, chronic superficial scaly acrodermatitis, chondrodermatitis and perioral dermatitis. This would also include autoimmune or drug induced dermatomyositis, or similar conditions associated with internal pathologies such as neutrophilic dermatosis, dermatomyositis or transient acantholytic dermatosis. Skin disorders also include those classified under eczema and associated with inherited or metabolic conditions including but not limited to ichthyosis, xerosis or asteatosis. And, dry skin conditions including psoriasis, lupus erythematosus, exfoliative keratolysis and any type of allergic inflammation of the skin such as urticaria.

The formula as a composite, is lethal to bacteria, fungus, mold and yeast and can be used to treat and/or prevent dermatological diseases in the presence or absence of the aforementioned symptoms, caused by various pathogens. Pathological skin conditions include those incurred by 1) yeasts; including but not limited to malassezia and candida 2) fungus; including but not limited to dermatophyte fungi; trichophyton, epidermophyton, microsporum, tinea and tinea affecting all areas of the body such as tinea barbae, capitis, corporis, cruris, manuum, pedis, and unguium 3) bacteria; including but not limited to those caused by staphylococci being folliculitis, furunculosis, staphylococcal scalded skin syndrome and streptococci being erysipelas, impetigo, necrotising fasciitis or ecthyma 4) parasites; including but not limited to mites, scabies and lice 5) molds; including but not limited to scopulariopsis, aspergillus, fusarium, scytalidinium 6) viral agents; including but not limited to coxsackie enterovirus, herpes, parvovirus, Epstein barr 7) any type of unknown skin disease such as Lichen planus and/or 8) any type of known or unknown skin disease to which there are no current effective treatments. The embodied invention may be useful as a multi-purpose ointment.

Preparation of the formula for the treatment and prevention of aforementioned skin disorder, may vary to achieve desired effects on the skin. While the best mode has not been investigated thoroughly, a working concentration base range has been established. Briefly, the formula is partially comprised of herbal components prepared by extraction procedure. A specified portion of each herbal plant (as indicated below) can be used, however this is not limited to experimenting with various other parts of the natural plant including the root, seed, nut, stalk, bark, vegetable, fruit, hull, bud, leaf, flower, bulb or entire. Pure fresh herbs are slowly dried at very low temperature, and macerated into an extract, typically comprised of one or more of the following: grain alcohol, distilled water, glycerine or vinegar. Extracts are the solvent in which herbal components are prepared, and may include any solvent that can be used to maximize therapeutic value, or commercial production feasibility at the discretion of one skilled in the art. These also include any liquid, chemical, alcohol, lipophilic oil based solvents or acetone. Depending upon the strength of the herbal extract, dry herb menstrumm ratios can vary (w/v) between 1:5-4:5. Typically herbal extracts are stored in a sterile closed container (glass or suitable), in a warm dry area, away from light for about 0.5-2 weeks with intermittent stirring. The extract is then filtered to remove particulates and stored at a cool temperature in an amber container to prevent exposure to light.

The herbal extracts are then combined with niacin and garlic, into a base carrier of pure aloe vera gel and optionally a dermatologically acceptable carrier. The development of a marketable skin care product would require incorporation of chemical ingredients that comprise a commercially feasible dermatologically acceptable carrier. These may include substances such as surfactants, binders, emulsifiers, stabilizers, preservatives, emollients, foaming agents, sweeteners, thickeners, surfactants, coloring agents, fragrances, lipids, additives, solvents, moisturizers, lubricants, carriers, bulking agents, deodorizers, buffers, or the like. Furthermore, the product as a whole may constitute a variety of delivery and product consistencies, including but not limited to, a suspension, solution, dispersion, lotion, liquid, gel, stick, capsule, foam, cream, pack, paste, coated glove or sock, spray, aerosol, ointment, sponge, gel cap, granule, bandage, gauze powder or any other type of bio-delivery system or improvements thereof. The ingredients that comprise a working example of the formula, as listed below are presented as % total weight herein specified as "% TW" with extended (EXT) ranges.

Working Example:

|  | % TW | EXT. Range (% TW) |
|---|---|---|
| Wormwood (*Artemisia Absinthium*) Extract | 9% | 0.5%-90% |
| Black Walnut Hull (*Juglans Nigra*) Extract | 9% | 0.5%-90% |
| Turmeric (*Curcuma Longa*) Extract | 7% | 0.5%-90% |
| Garlic (*Allium Sativum*) or Propolis Dry or Extract | 10% | 0.75%-70% |
| Licorice (*Glycyrrhiza Glabra*) Extract | 3% | 0.5%-25% |
| St Johns Wort (Hypericum) Extract | 3% | 0.5%-25% |
| Chamomile (*Matricaria*) Extract | 2% | 0.5%-25% |

-continued

Working Example:

|  | % TW | EXT. Range (% TW) |
|---|---|---|
| *Antibacterial Agent | 2% | 0.5%-25% |
| Niacin | 1% | 0.02%-5% |
| 100% Pure Aloe Vera or *DAC | 54% | 5%-95% |
| TOTAL | 100% | |

*DAC (Dermatological acceptable Carrier)
*Optional Antibacterial Agents Clove, Ginger, Nutmeg, Myrrh, Frankincense Both myrrh and frankincense are of the same botanical family bureraccac and both have antibacterial agents [See: Lakshmi et al. Chem Pharm Bull (Tokyo). 2003 September; 51(9):1081-4 and Dolara et al. Planta Med. 2000 May; 66(4):356-8.]. Therefore addition of similar herbs with similar bacteriostatic nature given the provision for option herbal antibacterial agents would not constitute new matter. Further, we have recntly done studies in our lab usingfrankincense, and found this herb to be equi-potent to myrrh. If examiner finds this to be new matter, we can delete it from the amended claims, and continue prosecution on the merits.

The formulation may vary with intended use, sensitivity of skin, age range, allergies, mammal species and illness classification. While a working example has been described above for human skin, alternative formulations may include preparation using fresh, dry, solid or aqueous preparations of active ingredients and variation in plant species amongst each genus. A larger concentration range could account for a therapeutically effective amount that may constitute a near pure solution of the active ingredients within the formula. Moreover, variation in formulation will be required to suit mammal species. For example, for treatment of feline skin disease, compounds such as aloe vera, garlic and wormwood are known to be toxic to cats, and would not be safe. Therefore, modification of the formula would be required, using ingredients such as turmeric and black walnut, which are safe and effective.

The best mode for carrying out the invention as described above, is not limited to the altering, substituting or adding of constituents, or variation in extraction procedures within the scope of the invention. To one skilled in the art, various modifications of the invention, without departing from the scope may include: 1) altering the % weight of each constituent 2) incorporating new components to optimize efficacy or commercial processing 3) altering the extraction time, conditions or temperature 4) introducing isolated chemical compounds derived from each plant extract individually or in combination to produce similar or better therapeutic results 5) or changing the formulation by subtracting aforementioned ingredients or using various combinations. The following is an elaboration on potential variation for each ingredient with extended ranges.

The formula may include pure, solids or extract of wormwood (*Artemisia Absinthium*), preferably derived from the aforementioned member the genus, but not limited to any species within the *Artemisia* genus, such as *Artemisia vulgaris, Artemisia annua, Artemisia biennis, Artemisia campestris, Artemisia dracunculus, Artemisia globularia, Artemisia kauaiensis, Artemisia Montana, Artemisia pontica, Artemisia rupestris, Artemisia sericea, Artemisia cana, Artemisia alpina* and *Artemisia maritime*. This constituent may be present between 0.5 to 90% TW, preferably ~9% TW.

The formula may include pure, solids or extract of Black Walnut (*Juglans nigra*), preferably obtained from the hull, kernal or leaf but also including any portion of the plant, preferably derived from the aforementioned member of the genus, but not limited to any species within the *Juglans* genus such as *Juglans* Regia. This constituent may be present between 0.5 to 90% TW, preferably ~9% TW.

The formula may include pure, solids, decolorized or extract of Tumeric Rhizome (*Curcuma Longa*), preferably derived from this member of the genus, but not limited to variation in species of the *curcuma* genus such as *Curcuma aromatica* and *Curcuma amada*. This constituent may be present between 0.5 to 90% TW, preferably ~7% TW.

The formula may include pure, solids or extract of St. Johns Wort (*Hypericum perforatum*), preferably obtained from the flower and bud, but also including any portion of the plant, preferably derived from the aforementioned member of the genus, but not limited to any species within the *Hypericum* genus such as *Hypericum acutifolium, Hypericum majus, Hypericum ascyron, Hypericum attenuatum* and *Hypericum formosum*. This constituent may be present between 0.5 to 25% TW, preferably ~3% TW.

The formula may include pure, solids or extract of Chamomile (*Matricaria Chamomile*), preferably obtained from the flower, but also including any portion of the plant, preferably derived from the aforementioned member of the genus, but not limited to any species within the *Matricaria* genus such as *Matricaria inodora Matricaria recutita, Matricaria occidentalis, Matricaria courrantiana, Matricaria perforata* or from the genus *Anthemis* including *Anthemis nobilis, Anthemis arvensis* and *Anthemis cotula*. This constituent may be present between 0.5 to 25% TW, preferably ~2% TW.

The formula may include pure, solids or extract of Licorice Root (*Glycyrrhiza Glabra*), preferably derived from the aforementioned member of the genus, but not limited to any species within the *Glycyrrhiza* genus such as *Glycyrrhiza glandulifera, Glycyrrhiza echinata, Glycyrrhiza aspera, Glycyrrhiza lepidota, Glycyrrhiza malensis* and *Glycyrrhiza uralensis*. This constituent may be present between 0.5 to 25% TW, preferably ~3% TW.

The formula may include deodorized garlic (*Allium sativum*), such as that described in (U.S. Pat. No. 4,933,201, Jun. 12, 1990, Sakai) or pure, powered, pulverized, minced or extract, preferably obtained from the bulb, but not limited to any portion of the plant, preferably derived from the aforementioned member of the genus, but not limited to any species within the *Allium* genus such as *Allium oleraceum, Allium ursinum, Allium ampeloprasum* and *Allium canadense*. This constituent may be present between 0.75 to 70% TW, preferably ~10% TW. The formula may include pure or extracts of propolis, as an optional ingredient to replace or be mixed with garlic, constituting between 0.75 to 70% TW, preferably ~10% TW.

The physical consistency of aloe vera may include solids, liquid or gels. The purity of aloe should be 100%, however lower purity may also be used. The base constituent (aloe vera or dermatologically acceptable carriers ) may be present between 5 to 95% TW, preferably ~54% TW.

Unlike other constituents of this formula that are applied topically, route of administration for niacin can be topical or oral, or both. Daily oral administration of niacin, nicotinic acid, niacinamide or chemical derivatives are within the range of 100-1000 mg/daily/human. For topical application, niacin, nicotinic acid, niacinamide or chemical derivatives of niacin, constitute a concentration between 0.02 to 5% TW, preferably ~0.75-1.0% TW.

Additional optional antibacterial herbal agents may be incorporated into the primary formula including dry, fresh, pure, or aqueous extracts of clove, nutmeg, ginger, or myrrh. This component may constitute a concentration of 0.5 to 25% TW, preferably ~2.0% TW. Optional herbs that may be incorporated into the primary formula, include those that are currently used for treatment of dry skin. These include one or more of the following: dry, pure or extracts of chickweed, burdock, nettle, horsetail, Pau D'Arco, blood root, buttercup, chickory, dandelion, echinacea, goldenseal, elecampane, arnica, horehound, lavender, meadowsweet, marigold, rosemary, sage, mountain grape, yarrow, eucalyptus, red clover, tea tree, lavender, yellow dock, calendula, red clover, myrrh, blackberry leaf and evening primrose. These optional constituents may constitute between 0.5 to 25% TWPAI, preferably ~2.0% TWPAI.

The formula is to be applied topically to the skin, in a number of doses and quantity of dose that is therapeutically effective in treating or preventing aforementioned skin disorders. Typically, the formula is generously rubbed in to the skin, and left to dry. Improved efficacy for severe skin conditions has been achieved by initially applying the topical ointment to the skin, and covering the skin with plastic gloves overnight. In the morning, the hands can be washed, and the formula applied throughout the day. Variation in topical application will depend upon extent of disease, sensitivity, therapeutic response, age, body weight, concentration and bioavailability of active ingredients. While the results from our study, indicate therapeutic value of this formulation, significant future research will be required to elucidate efficacy and possible allergic skin reactions that may occur in susceptible individuals. Previous research has indicated that dermatological side-effects can occur in select individuals in response to St John's Wort, aloe vera, chamomile and garlic (Ernst, E. Br J Dermatol 2000 143:923-9; de la Torre Morin, F., Sanchez Machin, I., Garcia Robaina, J. C., Fernandez-Caldas, E., Sanchez, Trivino, M. J Investig Allergol Clin Immunol 2001 11:118-22; Jappe, U., Bonnekoh, B., Hausen, B. M., Gollnick, H. Am J Contact Dermat 1999 10:37-9.). For this reason, a 48 H skin patch test on the armpit, and arm is advised before using. And, topical treatment to the site of injury should be scheduled in gradual dose increments.

This invention is not limited to any or all type of modifications to the embodied formula that are obvious to one skilled in the art, but not described in the aforementioned that adhere to the scope of the invention.

What is claimed is:

1. A topical skin care composition useful for treating dyshidrosis (pompholyx) and dry skin disorders, said composition comprising a therapeutically effective amount of:
    a) black walnut, wormwood, tumeric, garlic, wherein said garlic can be optionally substituted with propolis;
    b) two or more antibacterial/anti-inflammatory herbs selected from the group consisting of St. Johns wort, licorice, chamomile, clove, nutmeg, ginger, and myrrh;
    c) Aloe vera, alone or in combination with a dermatologically acceptable carrier, and;
    d) niacin, wherein said niacin further comprises niacinamide, and nicotinic acid.

2. The composition according to claim 1, wherein said black walnut comprises an extract derived from *Juglans nigra*, constituting between 0.5%-90% by weight of the total weight of the composition.

3. The composition according to claim 1, wherein said wormwood comprises an extract derived from *Artemisia*

*absinthium*, constituting between 0.5%-90% by weight of the total weight of the composition.

4. The composition according to claim 1, wherein said turmeric comprises extract derived from *Curcuma longa*, constituting between 0.5% to 90% by weight of the total weight of the composition.

5. The composition according to claim 1, wherein said garlic comprises an extract derived from *Allium sativum*, constituting between 0.75 to 70% by weight of the total weight of the composition.

6. The composition according to claim 5, wherein said garlic further embodies a physical form of one or more selected from the group consisting of maccrated, minced, diced, dried, pulverized, powdcred, deodorized and shredded.

7. The composition according to claim 1, wherein said propolis is combined with garlic, constituting collectively between 0.75 to 70% by weight of the total weight of the composition.

8. The composition according to claim 1, wherein said St. Johns wort comprises an extract derived from *Hypericum perforatum*, constituting between 0.5 to 25% by weight of the total weight of the composition.

9. The composition according to claim 1, wherein said licorice comprises an extract derived *Glycyrrhiza glabra*, genus, constituting between 0.5 to 25% by weight of the total weight of the composition.

10. The composition according to claim 1, wherein said chamomile comprises an extract derived from *Matricaria chamomile*, constituting between 0.5 to 25% by weight of the total weight of the composition.

11. The composition according to claim 1, wherein said clove, nutmeg, ginger, and myrrh comprises extracts derived from *Syzygium aromaticum, Myristica fragans, Zingiber officinale, Commiphora molmol*, respectively, wherein a combination of the two or more of these herbs constitute between 0.5 to 25% by weight of total weight of the composition.

12. The composition according to claim 1, wherein said Aloe vera alone or combined with a dermatologically acceptable carrier constitutes between 5-95% by weight of the total weight of the composition.

13. The composition according to claim 12, wherein said dermatologically acceptable carrier is comprises one or more selected from the group consisting of surfactarits, binders, emulsiliers, bulking agents, starches, additives, diluents, stabilizers, preservatives, emollients, foaming agents, gels, sweeteners, thickeners, vehicles, coloring agents, fragrances, solvents, moisturizers, lubricants, deodorizers and buffers.

14. The composition according to claim 13, wherein said dermatologically acceptable carrier is in a form of at least one selected from the group consisting of a suspension, solution, dispersion, lotion, liquid, gel, stick, capsule, foam, cream, pack, paste, coated glove or sock, salve, spray, aerosol, ointment, sponge, gel cap, granule, medicated bandage, mnedicated gauze, microparticles, nanospheres, microspheres, wipes, oil, powder and bio-delivery system.

15. The composition according to claim 1, wherein said dermatologically acceptable carrier comprises at least one selected from a group consisting of purified water, lanolin, lanolin alcohols, alcohols, vitamins, methylparaben, ethylparaben, butylparaben propylparaben, glycerin, vegetable oils, polysorbate, propylene glycol, para-aminobenzoie acid, mineral oil, carbomer, phospholipids, flour, starch, sorbitan laurate, carboxylic acids, triethanolamine, talc, titanium dioxide, antioxidants, gums, petrolatum, jojoba oil, isopropyl myristate, cetyl palmitate, sorbitan stearate, acids, base, cellulose, simethicone, butylated hydroxyanisole, butylated hydroxytoluene, glycol distearate, cetearyl alcohol, sorbitol, glyceryl stearate, cetearyl octanoate, dimethicone, wax, ethylenediaminetetraacetic acid, sodium lauryl sulfate, glyceryl dilaurate, quarteriurn-15, calcium sulfate, calcium chloride, metal salts, gelatin and imidazolidinyl urea.

16. The composition according to claim 2, wherein said black walnut constitutes about 9% by weight of the total weight of the composition.

17. The composition according to claim 3, wherein said wormwood constitutes about 9% by weight of the total weight of the composition.

18. The composition according to claim 4, wherein said turmeric
constitutes about 7% by weight of the total weight of the composition.

19. The composition according to claim 5, wherein said garlic constitutes about 10% by weight of the total weight of the composition.

20. The composition according to claim 7, wherein said propolis is
combined with garlic and constitutes collectively about 10% by weight of the total weight of the composition.

21. The composition according to claim 8, wherein said St. Johns wort constitutes about 3% by weight of the total weight of the composition.

22. The composition according to claim 9, wherein said licorice constitutes about 3% by weight of the total weight of the composition.

23. The composition according to claim 10, wherein said chamomile
constitutes about 2% by weight of the total weight of the composition.

24. The composition according to claim 11, wherein said combination
of at least two or more of clove, nutmeg, ginger, and myrrh constitute collectively about 2% by weight of the total weight of the composition.

25. The composition according to claim 12, wherein said Aloe vera alone or combined with a dermatologically acceptable carrier constitutes about 54% by weight of the total weight of the composition.

26. The composition according to claim 1, wherein said niacin niacinamide, and nicotinic acid constitutes about 1% by weight of the total weight of the composition.

* * * * *

UNITED STATES PATENT AND TRADEMARK OFFICE
CERTIFICATE OF CORRECTION

| | | |
|---|---|---|
| PATENT NO. | : 7,357,950 B2 | |
| APPLICATION NO. | : 10/801520 | |
| DATED | : April 15, 2008 | |
| INVENTOR(S) | : Elizabeth A. Mazzio and Karam F. Soliman | |

It is certified that error appears in the above-identified patent and that said Letters Patent is hereby corrected as shown below:

In the Specification

Column 1, line 14, please amend as follows:

This invention was made with government support under RCMI G12 RR 03020 which was awarded by the National Institutes of Health. The government has certain rights in the invention.

Signed and Sealed this
Twenty-seventh Day of October, 2015

Michelle K. Lee
*Director of the United States Patent and Trademark Office*